US006641566B2

(12) United States Patent
Douglas et al.

(10) Patent No.: US 6,641,566 B2
(45) Date of Patent: Nov. 4, 2003

(54) REUSABLE MEDICATION DELIVERY DEVICE

(75) Inventors: Joel Douglas, Los Altos Hills, CA (US); John Ramirez, Sunnyvale, CA (US); Robert Hugo, Gilroy, CA (US)

(73) Assignee: Sterling Medivations, Inc., Norcross, GA (US)

( * ) Notice: Subject to any disclaimer, the term of this patent is extended or adjusted under 35 U.S.C. 154(b) by 0 days.

(21) Appl. No.: 10/176,662

(22) Filed: Jun. 24, 2002

(65) Prior Publication Data

US 2002/0151855 A1 Oct. 17, 2002

Related U.S. Application Data

(63) Continuation of application No. 09/672,103, filed on Sep. 29, 2000, now Pat. No. 6,482,186.
(60) Provisional application No. 60/156,535, filed on Sep. 29, 1999, provisional application No. 60/170,570, filed on Dec. 13, 1999, and provisional application No. 60/177,762, filed on Jan. 24, 2000.

(51) Int. Cl.[7] ........................ A61M 5/135; A61M 1/00; A61M 37/00; A61M 5/20; A61M 5/00; A61M 5/178
(52) U.S. Cl. ..................... 604/218; 604/28; 604/135; 604/155; 604/181; 604/186; 604/191; 604/208; 604/211
(58) Field of Search ................ 604/28, 218, 135, 604/155, 181, 186, 191, 208, 211

(56) References Cited

U.S. PATENT DOCUMENTS

| 4,150,672 A | * | 4/1979 | Whitney et al. ........ 128/DIG. 1 |
| 5,505,704 A | * | 4/1996 | Pawelka et al. ............ 604/191 |
| 5,637,095 A | * | 6/1997 | Nason et al. ................ 604/135 |
| 5,891,087 A | * | 4/1999 | Ohtani et al. ................ 604/190 |
| 6,045,537 A | * | 4/2000 | Klitmose ..................... 604/224 |

FOREIGN PATENT DOCUMENTS

DK  WO 95/09021  *  4/1995  .......... A61M/5/315

* cited by examiner

Primary Examiner—William C Doerrler
Assistant Examiner—Filip Zec
(74) Attorney, Agent, or Firm—Burns, Doane, Swecker & Mathis, L.L.P.

(57) ABSTRACT

A medication injection or delivery system is provided for injecting fluids such as insulin within body tissue. The device includes a housing, a flexible shaft movably mounted within the housing, and a dose setting mechanism for controlling the movement of the shaft with respect to a fluid-containing cartridge removably positioned within or mounted to the housing. The flexible shaft, according to exemplary embodiments, includes a plunger and a flexible cable connected to the dose setting mechanism. The plunger and dose setting mechanism are connected together by the flexible shaft. The dose setting mechanism, in one aspect of the invention, includes a screw, a locking mechanism, and a nut assembly connected to the flexible shaft. The dose setting mechanism is used to set the dosage and prime the catheter. The plunger retracts into a recess to permit a new cartridge to be installed quickly.

15 Claims, 5 Drawing Sheets

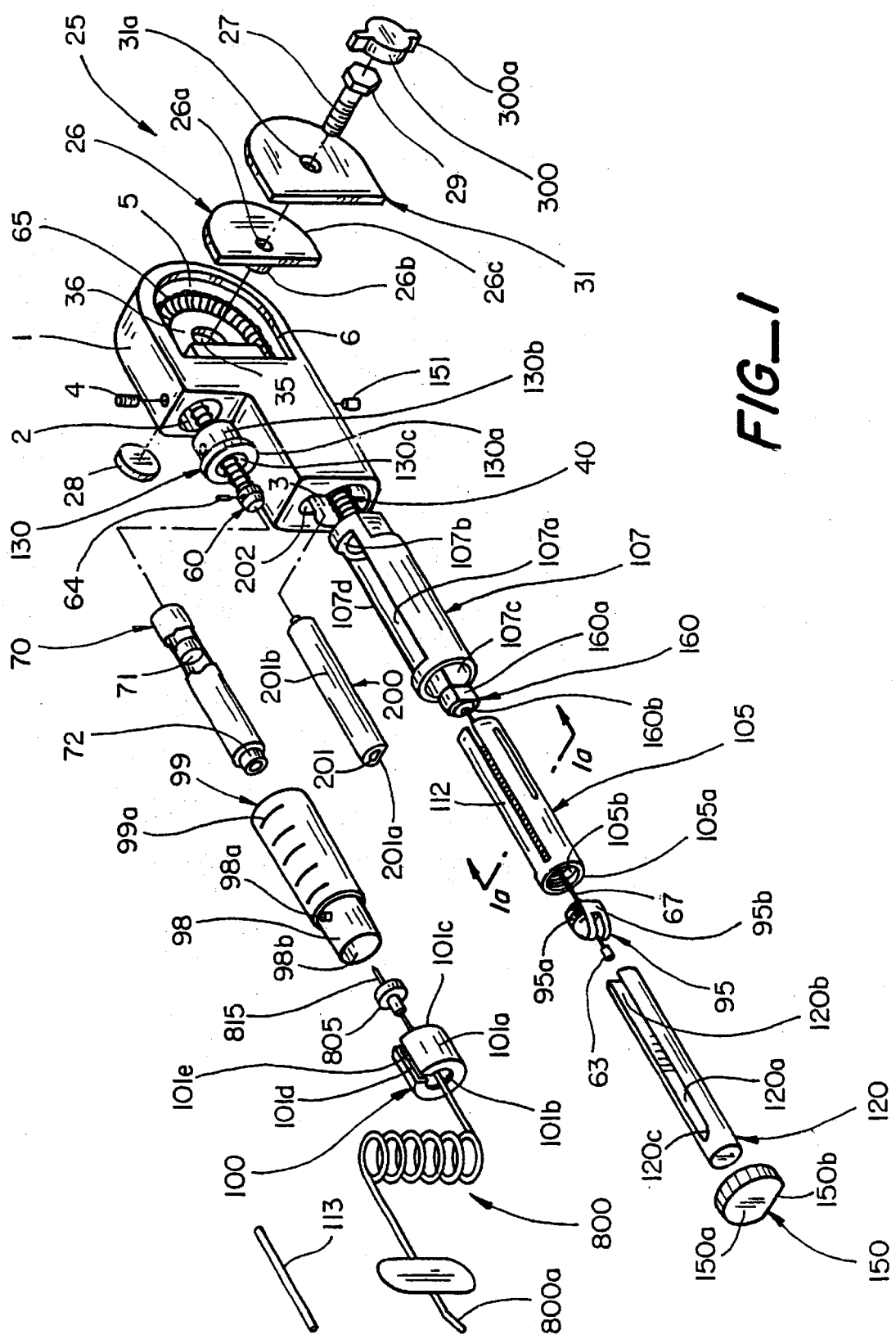
FIG_1

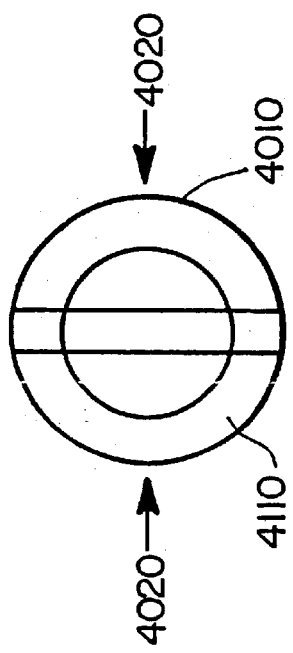
FIG_4
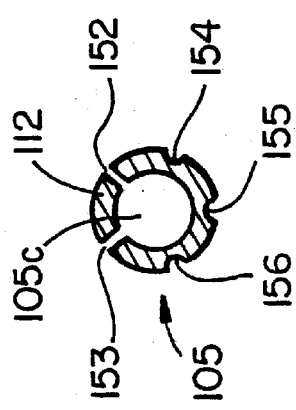
FIG_1a
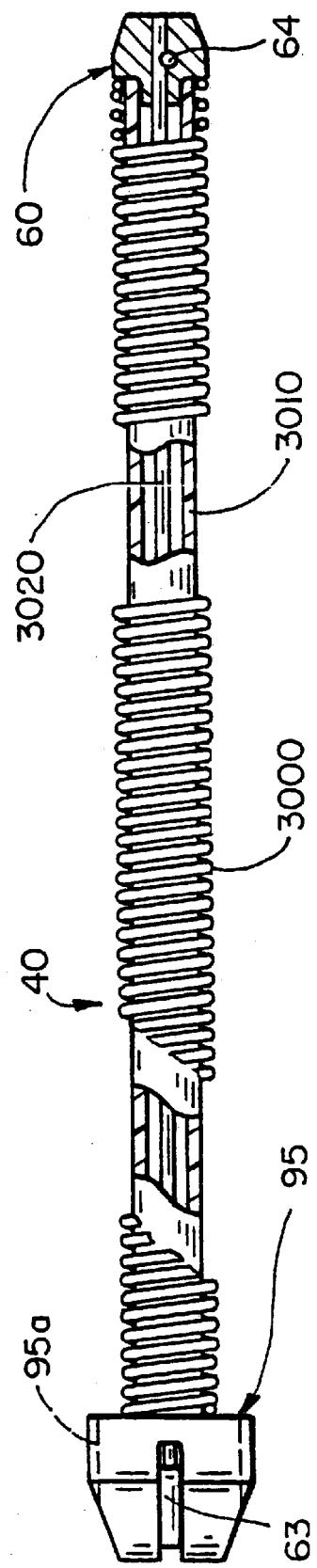
FIG_2

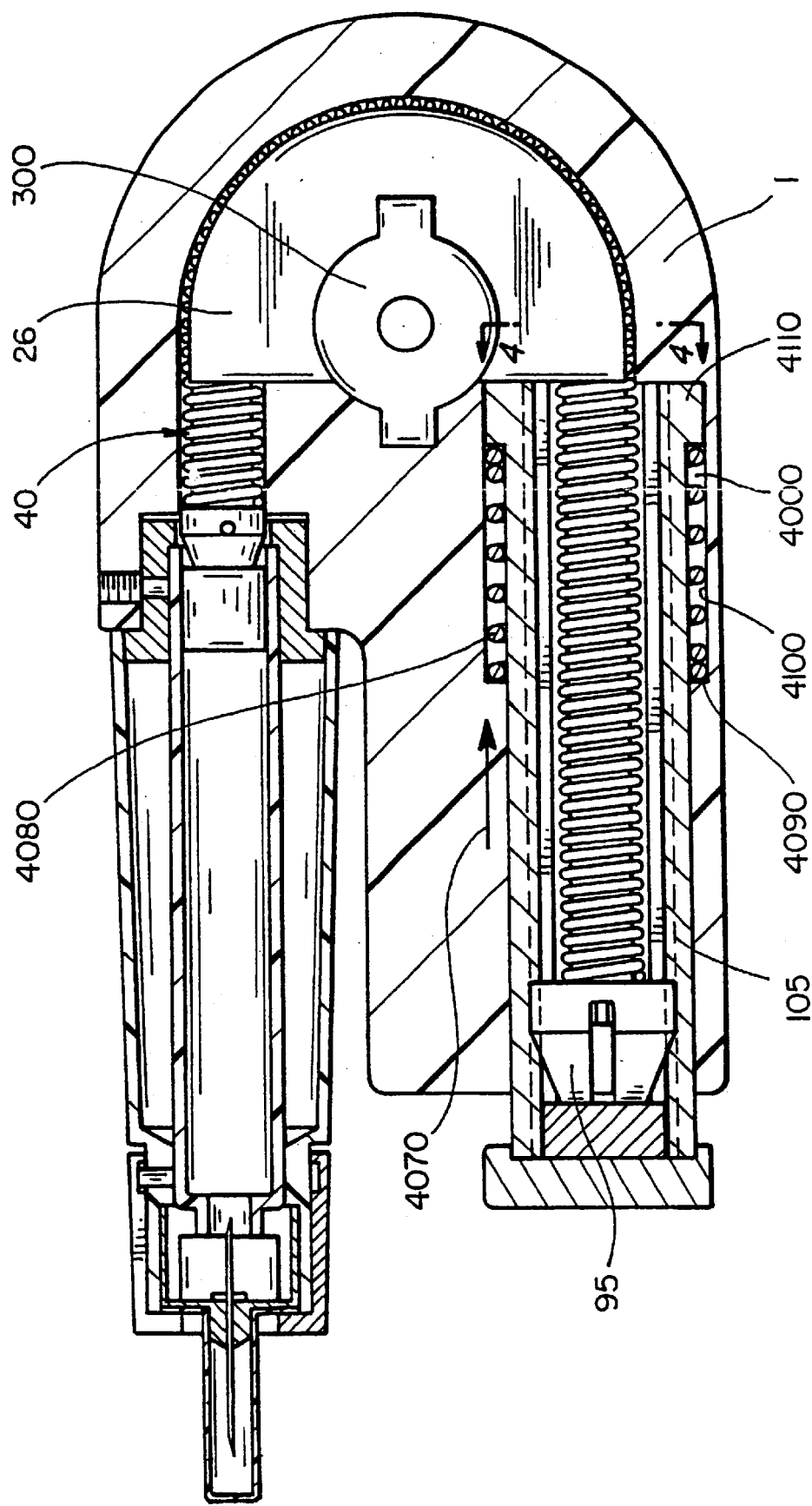
FIG_3

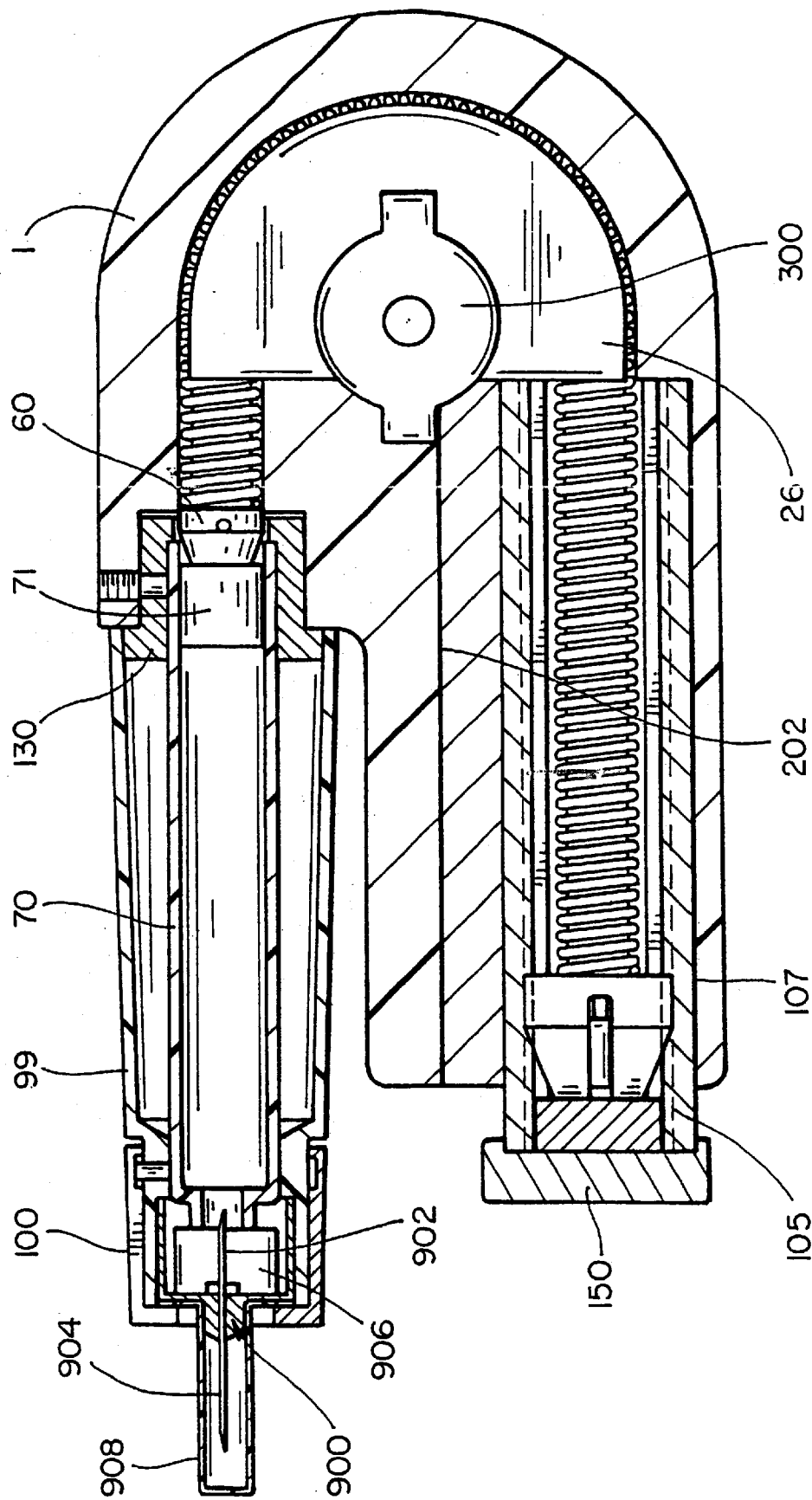
FIG_5

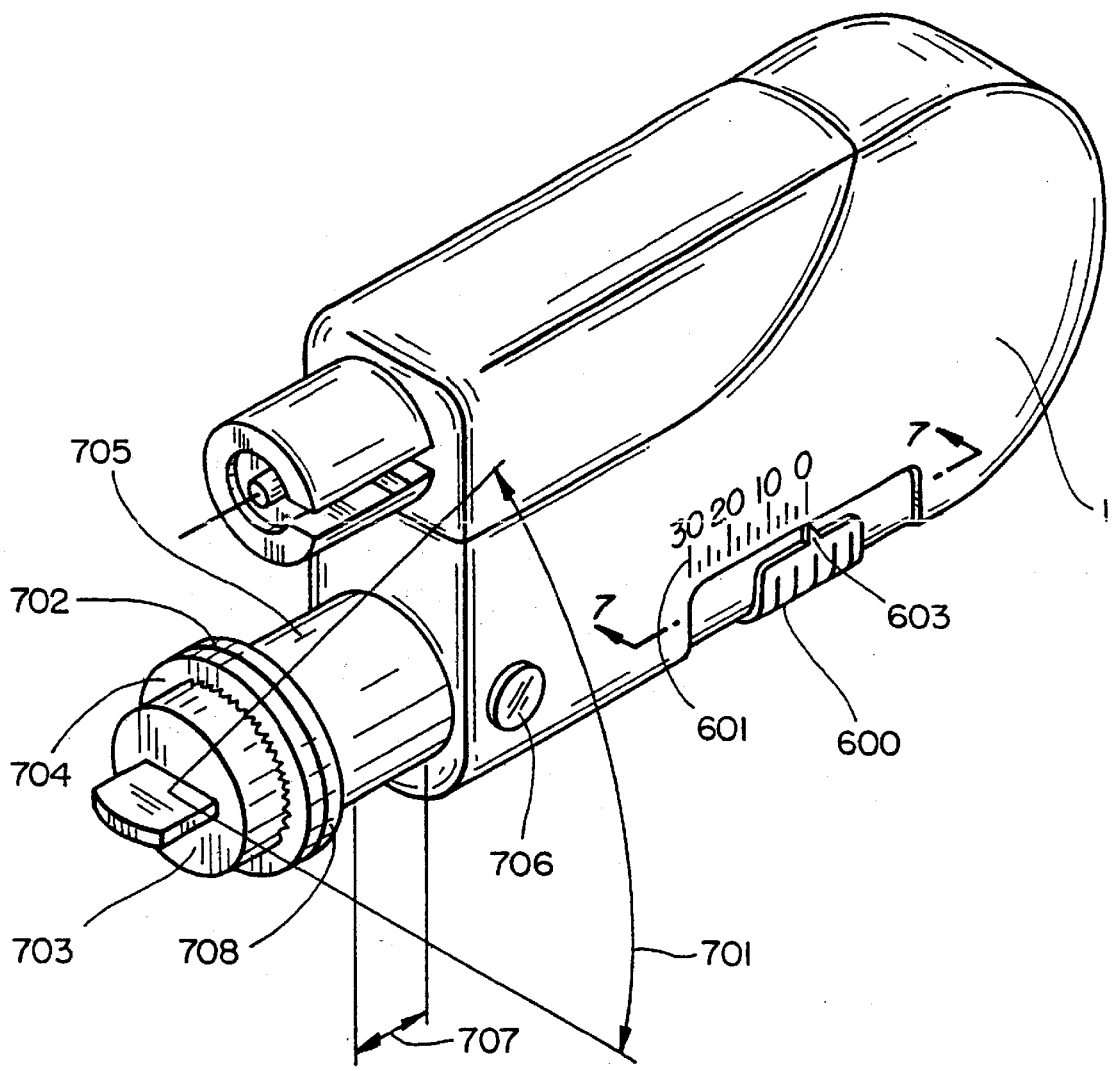
FIG_6
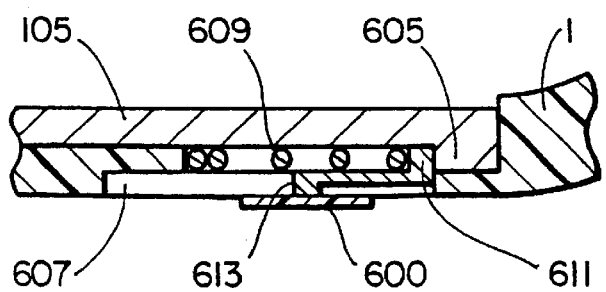
FIG_7

REUSABLE MEDICATION DELIVERY DEVICE

This application is a continuation of Application No. 09/672,103, filed on Sep. 29, 2000 now U.S. Pat. No. 6,482,186.

The present application is related to and claims priority under 35 U.S.C. §119 to U.S. application Ser. No. 60/156,535, filed Sep. 29, 1999, U.S. application Ser. No. 60/170,570, filed Dec. 13, 1999, and U.S. application Ser. No. 60/177,762, filed Jan. 24, 2000, the entire contents of each of which are incorporated by reference herein.

BACKGROUND OF THE INVENTION

1. Field of the Invention

The present invention relates to devices for delivering a predetermined amount of a substance to a patient, and more particularly to a manual medication delivery device. The present invention also relates to methods of use and kits including such devices.

2. Brief Description of the Related Art

There are many medical conditions that require the administration of liquid medicaments transcutaneously (through the skin) for prolonged periods. Diabetes, for example, may be controlled by daily, or more frequent, injections of insulin. The ability to administer numerous small dosages of insulin has been proven to be the best way to insure tight glucose control for a patient. The National Institutes of Health (NIH) conducted a long-term study of people with diabetes known as the Diabetes Complications and Control Trial (DCCT) were it was determined that the proper management of diabetes requires 4 or more injections of insulin per day. However, current devices either are not convenient or easy to use by patients. Syringes and insulin pens all require the patients to inject themselves and do not provide a convenient or discreet mechanism to accomplish medication delivery.

Since transcutaneous injections are painful and troublesome, and since each injection represents a possibility for infection, injections are spaced at intervals as far apart as possible, resulting in peak and valley concentrations of the medicament in the bloodstream or at the site in the body requiring the medicament, the peak concentrations occurring shortly after the administration of the medicament and the low, or valley, concentrations occurring shortly before the administration of the next injection. This method of administration exposes the patient to the possibility of overdose at peak levels and underdose at valley levels, but was nevertheless the standard method for many years in the absence of a better alternative.

Recently, systems have been developed in which a catheter is semi-permanently implanted in a patient to provide access to a transcutaneous site in a patient's body, and a liquid medicament is supplied to the catheter from a reservoir. Insigler and Kirtz (Diabetics, 28: 196–203, 1979) describe a portable insulin dosage regulating apparatus which uses an electrically driven mini-pump with an insulin reservoir to periodically dispense a predetermined number of insulin units (U). A small electronic control box is used to set the basal rate of 0.4 U/hr in stages of 0.2 U each. A switch is used to trigger a program that infuses a higher dose for a period of one hour, after which the system automatically goes back to the basal rate.

U.S. Pat. No. 3,963,380, issued Jun. 15, 1976, to Thomas et al., describes a micropump driven by piezoelectric disk benders. Although the pump draws only a small current, it requires a voltage of about 100 volts to drive the pump. Tamborlane et al. (The New England Journal of Medicine, 300: 573–578, No. 11, Mar. 15, 1979) describe a portable subcutaneous insulin delivery system which uses a battery driven syringe pump. The apparatus is bulky and heavy.

A peristaltic motor driven pump has been described by Albisser et al. (Med. Progr. Technol. 5: 187–193 [1978]). The pump weighs 525 g. and consumes 60 milliwatts at maximum pumping rates. This system has a continuous duty cycle. It is bulky and heavy and consumes a relatively large amount of power.

The pump devices that are currently commercially available require the patient to use a very intensive therapy that includes basal rate application of medication and periodic bolus injections. This type of therapy means the patient with diabetes must test their glucose levels to monitor and change the basal rate infusion and the bolus injections. This requires the patient to test frequently by lancing their finger and using expensive test strips to determine their glucose levels.

The inconvenience and difficulty needed to use current devices illustrates the need for a better mechanism to provide medication delivery for patients. This is especially true for those patients that have diabetes who are required to provide regular injections of insulin to treat their disease. In addition, the current problems that have recently been associated with oral medications will make the simplification of injection technology important for these patients who will be placed on insulin therapy to treat their disease since the current oral drugs are being removed from the market place.

SUMMARY OF THE INVENTION

According to a first exemplary embodiment, a portable infusion device comprises a housing having a cavity, a first opening into the cavity, and a second opening into the cavity, the cavity having a curved portion, an elongate flexible member, the flexible member being positioned at least in part in the curved portion, the flexible member being substantially axially incompressible and laterally flexible, and whereby, when a medication ampule including a piston is positioned adjacent to the first opening, the flexible member can be advanced through the curved portion of the cavity to push against and move the ampule piston without substantially compressing the flexible member.

According to a second exemplary embodiment, a portable infusion device comprises a housing having a proximal end, a distal end, a sidewall extending longitudinally between said proximal end and said distal end, an opening formed in at least one of said sidewall, said proximal end, and said distal end, and an interior cavity, an ampule positioned in said housing interior cavity, said ampule including a distal end having a sealed outlet, a piston in said ampule, and said ampule sized and configured to pass through said housing opening, a catheter having a proximal end, a distal end, and at least one lumen extending between said proximal end and said distal end, said catheter proximal end being releasably attached to one of said housing distal end and said ampule distal end, a longitudinally movable plunger positioned in said housing for engaging with and distally moving said ampule piston, manually movable dosage selection means, including interior portions positioned in said housing and selectively engaging said plunger, manually movable exterior portions positioned exterior of said housing for permitting a user of said portable infusion device to select a plunger travel distance, and a manually engageable element connected to said interior portions to move said plunger said plunger travel distance when said interior portions engage said plunger.

According to a third exemplary embodiment, a method of injecting a medication into a patient comprises the steps of providing a portable infusion device comprising a housing having a cavity, a first opening into the cavity, and a second opening into the cavity, the cavity having a curved portion, and an elongate flexible member, the flexible member being positioned at least in part in the curved portion, the flexible member being substantially axially incompressible and laterally flexible, positioning a medication ampule including a piston adjacent to the first opening, positioning a tube in fluid communication with the medication ampule and subcutaneously in a patient, advancing the flexible member through the curved portion of the cavity, pushing against and moving the ampule piston without substantially compressing the flexible member to dispense medication from the ampule, through the tube, and into the patient.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIG. 1 illustrates an exploded perspective view of a first exemplary embodiment of a device according to the present invention;

FIG. 1a illustrates a cross-sectional view of the device of FIG. 1;

FIG. 2 illustrates portions of a device in accordance with the present invention;

FIG. 3 illustrates a cross-sectional view of another embodiment in accordance with the present invention;

FIG. 4 illustrates an end elevational view of portions of the device of FIG. 3;

FIG. 5 illustrates a cross-sectional view of yet another embodiment in accordance with the present invention;

FIG. 6 illustrates a perspective view of yet another embodiment in accordance with the present invention; and FIG. 7 illustrates a cross-sectional view taken at line 7—7 in FIG. 6.

DESCRIPTION OF THE PREFERRED EMBODIMENTS

One advantage of capability of alternately using a catheter or a pen needle is unique to the invention because of the compact size, non-twisting attachment design, and positive adjustment capability. When the patient uses a catheter, the occurrence of infection and irritation is reduced because the medication, e.g., insulin, does not continuously enter the subcutaneous site. The patient can also use the device in a manner similar to currently available injection pens to delivery insulin when they do not want to use a catheter, thereby increasing the convenience of the device. By combining bolus therapy, catheter aided delivery, pen tip delivery, sanitary cartridge utilization, a reduction of injection site irritation, compact size, and the ability to select the method of delivery on a day-to-day basis, the patient is given many advantages by devices and methods of the present invention.

In general, a medication injection or delivery system is provided for injecting fluids such as insulin within body tissue. The device includes a housing, a flexible shaft movably mounted within the housing, and a dose setting mechanism for controlling the movement of the shaft with respect to a fluid containing cartridge removably positioned within or mounted to the housing. The flexible shaft, according to exemplary embodiments, includes a plunger and a flexible cable connected to the dose setting mechanism. The plunger and dose setting mechanism are connected together by the flexible shaft. The dose setting mechanism, in one aspect of the invention, includes a screw, a locking mechanism, and a nut assembly connected to the flexible shaft. The dose setting mechanism is used to set the dosage and prime the catheter. The plunger retracts into a recess to permit a new cartridge to be installed quickly.

The injection device includes elements threadably engaging the nut assembly to adjust the dosage of medication. According to other aspects of the present invention, a spring axially connected to the dosage setting nut is positioned so as to move the dosage setting nut when the brake assembly releases the flexible shaft connected to the nut assembly and the plunger. The dosage setting nut assembly that is engaged to the screw is stopped when the bottom of the dosage setting nut assembly comes into contact with stops on the housing or case. The device further includes elements for securing to the housing a cartridge containing fluid. The device alternatively does not have a spring connected with the dosage setting nut and the injection is accomplished by the patient manually providing pressure on the adjusting knob to inject the medication.

According to certain aspects of the invention, the flexible shaft is constructed of materials that can transmit both tension and compression. However, the flexible shaft should be capable of transmitting the forces around bends and curves, which insures that the device can be compact and discrete. The flexible shaft is capable of transmitting both tension and compression and also capable of being clamped by an external brake without the shaft being collapsed. The flexible shaft transmits the forces without axial deflection which would otherwise result in erroneous injection amounts. An outer spring provides compression resistance and an inner tube provides the ability for the spring neither to collapse when the brake is applied nor to distort when loaded axially in compression because it does not allow the windings to overlap each other when captivated in the guide tube. The cable provides the tension resistance for the flexible shaft assembly.

While it is contemplated that the present invention will utilize a standard insulin cartridge, holding 100–200 insulin units in a 1.5–3.0 milliliter volume, the present invention is not so limited, and can be resized and reconfigured to be used with medication cartridges or ampules of any size.

The ability to provide a small, discreet injection device that is capable of being used with both a catheter and an injection needle provides a significant advantage for the patient who must inject themselves on a regular basis, such as a person with diabetes. The patient can configure the device with a catheter on those occasions where discreet injection is needed, such as at work or other public situations. The catheter is then inserted subcutaneously and the medication is injected by setting the dosage mechanism and releasing or manually injecting the dosage. The catheter can be left in the patient for up to three days and thereby eliminates the need to insert a needle into themselves again over the three day period.

Devices of the present invention can have a small size and compact shape, which can allow the patient to wear it or hide it in their clothes so that it is not obvious to the people around them. The alternate configuration of being used with a conventional pen tip provides a means for the patient to use the same device to inject themselves when they do not want to use a catheter. The ability to use the device with two injection methods is unique and made possible by the system use of bolus therapy and the small and compact size.

The DCCT determined that the proper management of diabetes requires 4 or more injections of insulin per day. Currently, however, insulin-dependent diabetics rarely observe this critical treatment therapy because of the difficult and indiscreet nature of the current insulin delivery methods. All the available devices require the patient to carry the device and insulin, and inject in public. Those patients that use insulin pumps are afforded a more discreet means of infusion, but because of the basal rate therapy, require that they test their glucose levels 7 to 10 times a day. The present invention does not change the method of treatment but facilitates the delivery of insulin by providing a dual methodology to delivery the insulin that is selectable by the patient. They can either use a catheter or a pen-tip to deliver the required dosage of insulin. By creating a dual mode medication delivery device for the administration of a medicament, such as insulin, to a patient in small, controlled doses over an extended period the patients therapy is improved while maintaining a continuity with their existing means of treatment.

Referring to the drawing figures, like reference numerals designate identical or corresponding elements throughout the several figures.

FIG. 1 illustrates an exploded perspective view of a first exemplary embodiment of a device according to the present invention. The device includes elements for holding a medication ampule 70 so that it can be connected to a medication delivery tube of the user's choice, a housing 1 including elements for transmitting force to the piston 71 of the ampule, and elements with which the user can select a dosage of medication for delivery from the device and manually or automatically initiate administration of the medication. One aspect of the present invention is the provision of a force transmitting member which can effectively transmit force from dosage selection and manual administration elements along a non-linear path to the piston of the medication ampule, thus permitting the device as a whole to be constructed, and the constituent elements thereof arranged, in compact ways. The force transmitting member transmits the force without axial deflection, which would otherwise reduce dosage accuracy.

Turning back to FIG. 1, a sleeve 99 includes a hollow interior sized to receive a medication ampule 70 therein through an opening 98b in a cylindrical extension 98 of the sleeve. The sleeve 99 preferably is transparent or translucent and preferably includes dosage indicia thereon so that the user may visually inspect the contents of the ampule vial and determine the amount of medication therein. The extension 98 includes an upstanding peg 98a set back from the opening 98b. The peg 98a cooperates with a circumferential groove 101e formed on the interior of a slip collar 100. When the slip collar is slipped over the extension 98 with the peg 98a extending through a longitudinal slot 101d in the sidewall 101a of the slip collar, the peg may enter the groove 101e. With the peg in the circumferential groove, the slip collar 100 can be rotated, securing the slip collar to the extension 98 against longitudinal movement.

The cooperation of slip collar 100 and extension 98 permits a needle holding device, described below, to be placed in and secured between the slip collar and the extension. While many needle holding devices are within the spirit and scope of the present invention, exemplary embodiments will now be described. For example, a subcutaneous infusion set 800 can be secured between the slip collar 100 and the extension 98 to fluidly communicate the interior of the medication ampule 70 with a subcutaneous needle 800a on the distal end of the subcutaneous set 800. The proximal end of the set 800, as will be readily appreciated by one of ordinary skill in the art, includes a needle or other septum piercing element 815 with an associated hub 805 at the proximal end of the set. The hub 805 has an outer diameter smaller than the interior diameter of the slip collar 100, yet larger than the inner diameter of a distal opening 101b of the slip collar, so that he slip collar will hold the hub and piercing element 815 in place. The piercing element 815 has a length and diameter so that when the hub 805 and piercing element 815 are retained by the slip collar 100 within the hollow interior of the extension 98, the piercing element pierces the septum 72 at the distal end of the medication ampule 70. Thus, the slip collar 100 and extension 98 secure the proximal end of the set 800 to the ampule 70 and place the subcutaneous needle 800a in fluid communication with the interior of the ampule through the septum 72. The hub 805 applies a sufficient pressure to the septum 72 when engage to the septum to minimize deformation of the septum when the piston 71 is engaged.

Instead of subcutaneous set 800, the subcutaneous injection set described in Attorney Docket No. 032994-013, 09/675,159 filed Sep. 29, 2000, entitled "Subcutaneous Injection Set for Use with a Reservoir that has a Septum", Joel Douglas et al., which is incorporated by reference herein, can be used. Further optionally, the adapter described in Attorney Docket No. 032994-017, 09/672,097 filed Sep. 29, 2000, entitled "Pen Needle Assembly and Adapter", Joel Douglas et al, which is incorporated by reference herein, can be used. Also optionally, the adapter described in Attorney Docket No. 032994-019, 09/672,456 filed Sep. 29, 2000, entitled "Micro Infusion Device", Joel Douglas et al, which is incorporated by reference herein, can be used.

An advantage of the present invention is that, when used with an administration set which includes a length of tubing, such as tubing 800b, between a piercing element and the needle (e.g., needle 800a) which is inserted into the user, the tubing can effectively act as a strain relief for the junction of the piercing element 815 and the septum 72, the junction of the needle 800a and the user's skin, or both. Thus, the septum 72 is less prone to be distorted by the piercing element 815, and thus can increase the accuracy of the dosage administered and assist in maintaining the sterility of the contents of the medication ampule 70. Similarly, the user's skin is less prone to be pulled during injection, which can improve the user's comfort levels.

The exemplary device illustrated in FIG. 1 includes a housing 1 that has an interior cavity 5 that accommodates a flexible shaft 40. The flexible shaft 40 will be described in greater detail below and with reference to FIGS. 2 and 3. Flexible shaft 40 is slidably movable in the cavity 5 so that it can extend out of the housing in order to push on the piston 71 of the ampule 70, and in this manner acts as a plunger for the piston. The flexible shaft is constructed so that it is capable of transmitting force to the piston 71 to expel medication from the ampule 70, but the flexible shaft is also flexible so that it can be used in a bent configuration. The provision of the flexible shaft therefore enables the design of the housing of devices according to the present invention to be more compact than traditional "pen-type" injectors, while allowing accurate injections to be made, because axial deformation of the flexible shaft is minimized.

The housing 1 includes openings 2 and 3 that lead to the cavity 5. A fitting 130 is positioned in the opening 2, and includes a hollow interior 130c, a cylindrical body 130b, and an annular flange 130a on one end of the fitting. As can be seen in FIG. 1, the hollow interior 130c is sized so that the flexible shaft 40 can slide through the fitting 40. The fitting is secured to the housing by, e.g., glue, ultrasonic welding, a screw 4, or the like.

A brake mechanism 25 is also optionally provided to permit a user of the device to releasably hold the flexible shaft 40 from advancing into the ampule and dispensing medication. A seat 36 is formed or positioned in the housing 1, and includes a transverse hole 35 through the housing. A generally D-shaped brake shoe 26 includes a threaded hole 26a and a tubular extension 26b which is received in the hole 35 with some clearance so that the extension can rotate in the hole. The housing 1 includes a transverse opening 6 which can be closed by a cover 31 having a hole 31a. A threaded bolt 27 with a head 29 is threaded through the cover's hole 31a and into the threaded hole 26a. A cover 28 is secured to the back side of the housing to cover the other side of hole 35. A knob 300 having ears 300a is secured to the head 29 to permit a user to rotate the bolt, and therefore the brake shoe 26. The shoe 26 is configured so that the upon rotation about an axis extending through hole 26a and bolt 27, the outer curved portion 26c is rotated out farther away from the hole 26a and engages and presses against the outer surface of the flexible shaft 40. Further rotation of the shoe 26 causes the shoe to press against the flexible shaft 40 with a force sufficient to hold the shaft in place from displacement along the length of the shaft. Rotation of the shoe 26, by rotation of the knob 300, in the opposite direction disengages the curved portion 26c from the flexible shaft 40, permitting the shaft to move.

The device also includes a set of elements which permit the user of the device to set a medication dosage and drive the flexible shaft 40 to dispense and administer that dosage. For ease of illustration in FIG. 1, some portions of the flexible shaft 40 have been removed from the illustration, but it is to be understood that the embodiment of the flexible shaft illustrated and described herein extends continuously between a plunger end attached to plunger 60 and another, opposite end secured to nut 95.

The nut 95 includes partial threads 95a on the top of the nut, and is connected to the flexible shaft 40, e.g., by a swag 63. The threads 95a do not extend all the way around the nut, but rather are only present on a portion so that the nut can engage and disengage with a sleeve 105, as described in greater detail below. The nut therefore can include sidewalls 95b which are sized and configured so as not to mate with the interior threaded surface 105b of the sleeve 105. According to one aspect of the present invention, the nut 95 is attached to a tension cable 67, which forms a part of the flexible shaft, described in greater detail below. The nut 95 is positioned in the sleeve 105 and the sleeve can rotate around the nut when the threads of the nut and sleeve are engaged. The pitch of threads 95a is selected so that a desired fraction or number of rotations of sleeve 105 relative to nut 95 corresponds to a desired dosage of medication dispensed from the ampule 70. As will be readily appreciated by one of ordinary skill in the art, threads 95a can be single or multistart threads.

The sleeve 105 includes, as discussed above, a hollow interior 105c and has an interior surface which includes threads 105b to mate with the exterior threads on nut 95. As better illustrated in FIG. 1a, the sleeve 105 optionally further includes slits 152, 153 through the wall of the sleeve. The slits 152, 153 define a tab or finger 112 which can flex away from the nut 95, thus disengaging the threads of the sleeve 105 and the nut 95. Deflection of the tab or finger 112 allows a user to push on plunger 60 to retract the nut 95 in sleeve 105. The exterior surface of the sleeve 105 also preferably includes one or more equally circumferentially spaced, longitudinally extending grooves 154, 155, 156. When the slits 152, 153 are provides, they act as additional grooves and are preferably equally spaced with the grooves 154, 155, 156. When the slits 152, 153 are not provided, additional grooves are provided in their places. The grooves and slits cooperate with one or more small pins or similar protuberances 151 to generate an audible click, a tactile snap, or both, when the sleeve 105 is rotated within the housing 1. Preferably, the number and spacing of the grooves 154, 155, 156 is selected along with the pitch of the threads 95a, 105b so that the circumferential distance between the grooves corresponds to a known portion of a desired dosage. By way of example and not of limitation, threads 95a, 105b and the circumferential spacing of grooves 154, 155, 156 can be selected together so that one unit of medication from ampule 70 is dispensed for each audible/tactile click generated by the interaction of pins 151 and the grooves.

A dosage knob or dial 150 is secured to the outer end 105a of the sleeve 105 so that rotation of the knob 150 rotates the sleeve. When assembled (see, e.g., FIG. 3), the knob 150 is outside of the housing 1, while the sleeve 105 moves in and out of the cavity 5 through the opening 3. A motion limiting element 120 is positioned in the sleeve 105 and partially around the nut 95. In the exemplary embodiment illustrated in FIG. 1, the motion limiting element takes the form of a split shaft having a longitudinally extending slot 120a that extends transversely through the shaft. The slot 120a can be, for ease of assembly, open at the end 120b of the shaft. The transverse width of the shaft 120 is selected to be smaller than the internal diameter of the sleeve 105 in which the shaft is positioned so as not to interfere with the rotation of the sleeve relative to the nut 95. The dimensions of the slot 120a are selected so that the nut 95, as well as the flexible shaft 40 secured to the nut 95, can move longitudinally along the shaft without the shaft interfering with this movement. The length of the slot 120a is selected, however, so that the closed end 120c of the slot 120 prevents the nut 95 from being backed out of the sleeve 105. Further preferably, the length of the slot 120a is selected to correspond to the maximum dosage amount that it is desired to dispense from ampule 70. For example, the length of the slot 120a can be selected to be a preselected percentage of the total distance that piston 71 can travel in ampule 70, up to 100% of the travel distance. As illustrated better in FIG. 3, the length of the flexible shaft 40 is selected so that the nut 95 is positioned adjacent to the closed end 120c when a new ampule is installed in the device.

A second retaining sleeve 107 is also positioned in the cavity 5. The sleeve 107 is mounted in the housing 1 so that an open outer end 107c of the sleeve is adjacent to the opening 3. The sleeve 107 includes a hollow interior 107a. The inner end of the sleeve 107 includes an opening through which the flexible shaft 40 extends which is delimited by a stop 107b. An insert 160 is mounted in the stop 107b. The insert 160 includes flats 160a which are sized to receive the end 120b of the shaft 120, and the shaft is secured to the insert. The insert also includes a hollow interior 160b through which the flexible shaft 40 extends.

According to yet another embodiment of the present invention, the housing 1 can further include a recess 202 adjoining that portion of the cavity 5 which contains the sleeve 107. A cylindrical locking member 200 is rotatably positioned in the recess 202. The member 200 includes a flat exterior portion 201a, a cylindrical exterior portion 201b, and a keyhole, recess, or the like 201 in the external face of the member. The sleeve 107, in this additional embodiment, includes a cutout portion 107d on that portion of the sleeve which faces the recess 202. Recess 202, member 200, and cutout portion 107d are provided to cooperate with tab 112, as described in greater detail below, to permit rapid retraction of the flexible cable 40 and nut 95.

Turning now to FIG. 2, one embodiment of the flexible shaft 40 is illustrated with portions broken away. According to the embodiment illustrated in FIG. 2, the flexible shaft 40 includes an outer flexible spring 3000, an intermediate flexible tube 3010 positioned inside the spring 3000, and an inner tension cable 3020 positioned inside the tube 3010. The outer diameter of the intermediate tube 3010 is preferably selected to be slightly smaller than the inner diameter of the spring 3000 so that the tube supports the spring along its entire length, while permitting the spring and tube together to bend without kinking. The tube 3010 also prevents the spring windings from overlapping one another. The inner tension cable 3020, which corresponds to element 67 in FIG. 1, extends between the plunger 60 and the nut 95. The cable 3020 is secured to the plunger 60, such as by screw 64, and to nut 95, as by the swag 63. The tension cable 3020, through the plunger 60 and the nut 95, prevents the spring 3000 from extending, yet is flexible to also bend and flex with the spring and the tube 3010 to transmit force along a linear or non-linear path to the piston 71 of the ampule 70 without axial deformation.

According to one embodiment, the flexible shaft 40 includes a spring segment available from Century Spring of Los Angeles, Calif., model E-12, which has a wire size of at least 0.035 and an outer diameter winding width of 0.25 inches. The intermediate tube can be formed of a PVC tube with an outer diameter of 0.176 inches and inner diameter of 0.100 inches. A stainless steel cable of 0.035 inches outer diameter is threaded through the PVC tube and used to place the assembly under compression.

The operation of the embodiments illustrated in FIGS. 1, 1a, and 2 will now be described with reference thereto and to FIG. 5, which illustrates a cross-sectional view of the assembled device. FIG. 5 illustrates the device and an ampule 70 positioned therein prior to the administration of medication from the ampule, and with the flexible shaft 40 completely retracted. The user locks the flexible shaft 40 by rotating the knob 300. The user than rotates the knob 150, which rotates the sleeve 105. Audible and/or tactile clicks are produced by rotation of the sleeve relative to the housing 1. As the sleeve 105 is rotated, the sleeve 105 moves out of the housing 1 while the nut 95 remains stationary. In this manner, the sleeve is backed out of the housing a distance which relates to, and is preferably the same as, the distance that the piston 71 will be moved.

When the user has backed out the sleeve 105 the desired amount, as preferably indicated by the audible and/or tactile clicks, or by visual inspection, the user turns the knob 300 to unlock the flexible shaft 40 and to permit it to move. The user then presses on the flat face 150a of the knob, which pushed the sleeve 105 in toward the housing. Because the threads 105b of the sleeve 105 mate with the threads 95a of the nut 95, and the nut is secured to the flexible shaft 40, the nut 95 is driven along with the sleeve toward the housing.

This movement of the nut 95 and sleeve 105 continues while the user presses on the face 150a. The flexible shaft 40 pushed by the nut 95 through the cavity 5 and through the fitting 130. The plunger 60 on the plunger end of the flexible shaft 40 pushes against the piston 71 of the ampule 70, which in turn expels medication from the ampule. The ampule 70 is held in the device by split collar 100, and therefore the force generated by the user against face 150a is transmitted through the sleeve 105, nut 95, flexible shaft 40, and plunger 60 to the piston 71.

As the flexible shaft 40 is free to move along its own length in the cavity 5, but restrained from buckling by the housing 1, the direction of the user-generated force is changed but still transmitted to the piston. Upon completion of the desired administration, the knob 150 is again adjacent to the housing 1, as illustrated in FIG. 5. The entire device can then conveniently be placed in a carrying case, handbag, pocket, or wherever the user desires, while permitting the subcutaneous set 800 to remain in place inconspicuously attached to the infusion device.

When the user desires to administer another volume of medication from the ampule 70, the plunger 60 is still in position against the piston 71 from the previous administration. The nut 95 is in a position between the end 120c and the end 120b of the shaft 120, having been moved as a result of the prior advancement of the flexible shaft 40. The knob 150 is again rotated, backing out the sleeve 105, and the flexible shaft 40 is again advanced through the housing 1 to push the piston 71.

Devices according to the present invention function to preserve the information of how much of the medication a user desires to dispense from the ampule, even when there less than this amount contained in the ampule installed in the device. That is, devices according to the present invention have a memory aspect which retains information about how much of a dosage is left to be administered even if the ampule must be changed to complete the administration. By way of example, if the user backs out the sleeve 105 a distance which corresponds to the administration of 10 units of medication, but the position of the piston 71 in the ampule only will permit 7 units of medication to be dispensed, the sleeve 105 and flexible shaft 40 will only travel the distance to dispense the 7 units. Thus, the knob 150 will not be moved up to housing 1, and the user will have an indication that the entire desired dosage has not been administered. By providing the device with a dosage indicator, described in greater detail below, the user can see how much additional medication must be administered for a complete dosage. The user can load a new ampule into the device, dial out an appropriate supplemental dosage amount, and complete the dosage administration.

When the flexible shaft 40 has been moved so that the nut 95 is against the insert 160, the shaft must be retracted to reset the device. This can be accomplished several ways. The knob 150 can be retracted fully, pulling the nut with it, and then the knob 150 rotated to advance the sleeve 105 into the housing while the nut 95 remains stationary. The provision of locking member 200, recess 202, and cutout 107d permits another way of resetting the device. A tool 113 is provided which includes an end which can be inserted into recess 201a to rotate the locking member 200 in the recess 202. The knob 150 is pulled out as far as it will, which retracts the nut 95 and the flexible shaft 40. The knob 150 is then rotated so that an indicator, such as flat 150b opposite and aligned with slot 120a, shows that the tab 112 is adjacent to and aligned with the cutout 107d and recess 202. The tool 113 is then used to rotate the locking member 200 in recess 202 so that the flat 201a is aligned with and adjacent to the tab 112. Thus, the tab is no longer restrained against radial movement, and can deflect outward in response to relative movement of the nut 95. The knob 150 is then pushed in, which causes the sleeve 105 to move in toward the housing. Because the tab 112 is aligned with the cutout 107a and the flat 201a, the tab can deflect outward, disengaging the threads 105b from the threads 95a of the nut 95. The sleeve 105 therefore moves inward relative to the nut 95, with the result that the nut moves to a position closer to end 105a of the sleeve. If the nut 95 is not yet adjacent to the end 105a, this process can be repeated to move the sleeve 105 and nut 95 relative to each other to reset the device.

FIGS. 3 and 4 illustrate yet another embodiment in accordance with the present invention. The device illustrated in FIGS. 3 and 4 is similar in some respects to those illustrated in FIGS. 1–2, and therefore only the differences between them will be described herein. The embodiment of FIGS. 3 and 4 include structures which provide an automatic injection function. The housing 1 includes the cavity 5 having an additional space 4000 radially outside the space in which the sleeve 105 extends. The sleeve 105 includes an annular shoulder 4110 which slides in the space 4000. A spring 4080 is also positioned in the space 4000 between the shoulder 4110 and a shoulder 4090 of the housing which delimits the space.

FIG. 4 illustrates an end view of the shoulder 4110. The sleeve 105 includes portions 4010 which act as spring cams against the inner surface 4100 of that portion of the housing which defines the space 4000. Thus, friction is developed between the housing and the shoulder 4110. According to another aspect of the invention, the profile of the surface 4100 is slightly tapered so that the frictional force between the shoulder and the surface changes.

In operation, the device illustrated in FIGS. 3 and 4 is used in a manner very similar to that described above with respect to FIGS. 1–2. When the sleeve 105 is backed out the desired amount, the spring 4080 is compressed, and exerts a force in the direction of arrow 4070 against the sleeve 105 through the shoulder 4110. When the user wants to deliver the dosage, the knob 300 is rotated, unlocking the flexible shaft 40. The spring 4080 pushes against the shoulder 4110, driving the sleeve 105, nut 95, and flexible shaft 40 as described above. The friction between the shoulder 4110 and the surface 4100, which acts against the motion of the sleeve in the direction opposite the arrow 4070, slows the sleeve 105. The taper of the surface 4100 and the elasticity of the spring cams 4010, generated by the normal force 4020 of the spring cams against the surface 4100, cause the frictional force to change over the travel of the shoulder 4110, thus regulating the speed of the injection. Preferably, the surface 4100 is tapered so that the frictional force is higher at the beginning of the injection stroke and less toward the end of the injection stroke.

FIG. 5 illustrates other aspects of the present invention, and portions of the elements illustrated in FIG. 5 have been described elsewhere herein. FIG. 5 also illustrates another embodiment of a device for administering the dosage to the user, a pen needle 900. Pen needles usable in the present invention are currently commercially available, for example a Novofine® 30⅓ inch (8 mm) pen needle (Novo Nordisk, Princeton, N.J.). As illustrated in FIG. 5, the pen needle 900 includes a needle 902 for piercing the septum 72, a needle 904 for insertion subcutaneously into the patient in fluid communication with the needle 902, and a cylindrical shroud or cover 906 which covers the needle 902. The shroud 906 is placed over the septum 72, which pushes the tip of the needle 902 into the interior of the ampule 70. The split collar 100 is placed over the pen needle 900, securing it in place. A cap or cover 908 covering the needle 904 is then removed, the needle inserted into the user, and the dosage can be delivered to the user.

FIG. 6 illustrates yet another embodiment of a device in accordance with the present invention. The device illustrated in FIG. 6 is similar in some respects to other embodiments described herein. The device includes a mechanism 700 which permit the user of the device to establish a zero set point on a scale, so that the user can then set a proper dosage amount for administration. A sleeve 705 is mounted around the outer end of the sleeve 105 (see FIG. 1) and includes a set of numbers printed on the external surface of the sleeve 705. The sleeve 705 includes an outer ring 708 which is adjacent to a ring 704 on the dosage setting knob 703 (which corresponds to knob 150) of the sleeve 105. The rings 704 and 708 include mating structures, such as complementary teeth, so that when the rings are held together, they will rotate together without slipping. A spring 702 is positioned between the rings 704 and 708 to bias the outer sleeve 705 outward so that the rings abut each other. The outer sleeve extends into the housing 1 through which, with the aid of a magnifying glass type window 706, the user can view the numbers printed on the exterior of the sleeve 705. The spacing of the numbers on the sleeve 705 is selected so that a relatively large angular rotation 701 of the dosage setting knob 703 is matched with the appropriate distance of linear motion 707 of the sleeves 705, 105.

To use the zero scale, the user pushes the outer sleeve 705 in toward the housing against the force of the spring 702, disengaging the complementary structures on the rings 704, 708. The outer sleeve 705 can then be freely rotated until a zero appears in window 706. The user then releases the sleeve, which returns to its position with the rings 704, 708 next to each other. The user can then manipulate the dosage knob 703 to back out sleeve 105, which carries with it sleeve 705 because of the engagement of rings 704 and 708. Therefore, the outer sleeve 705 is rotated and moved further out of the housing 1, moving the appropriate number printed on the exterior of sleeve 705 beneath window 706 for the user to verify that the dosage knob has been set to administer the correct dosage.

FIGS. 6 and 7 illustrate yet a further embodiment of the present invention. A side injection actuator 600 is movably mounted to the side of the housing 1, and is connected (see FIG. 7) to portions of the sleeve 105. The actuator 600 includes a scale indicator 603 which aligns with a scale 601 printed on the exterior of the housing. As illustrated in FIG. 7, which illustrates a partial cross sectional view through the housing at line 7—7, the housing includes a slot 607 in which a connecting arm 613 slides. The arm 613 connects together the actuator 600 and a ring 611 which is received in the same space as the spring 609 (corresponding to spring 4080). As will be readily appreciated by one of ordinary skill in the art, spring 609 and the automatic injection feature can be optionally removed. The ring 611 abuts against an outwardly extending shoulder 605, similar to shoulder 4110, formed on sleeve 105.

The side injection actuator 600 moves along with sleeve 105 as the sleeve is backed out of the housing 1 when the user sets a dosage amount with dosage knob 150 or 703, because the ring 611 is pushed linearly backward by the shoulder 605. As the ring 611 and shoulder 605 are not attached, however, the rotation of shoulder 605 as the sleeve 105 is backed out does not cause the ring 611 to rotate. Once the user has set a dosage amount, the user can choose between pushing on the dosage knob 150 or 703, or pushing the side injection actuator forward along the housing toward the position illustrated in FIG. 7. The scale 601 and scale indicator 603 provide a visual check for the user that the dosage amount has correctly been set.

While the invention has been described in detail with reference to preferred embodiments thereof, it will be apparent to one skilled in the art that various changes can be made, and equivalents employed, without departing from the scope of the invention. Each of the foregoing references and documents are incorporated by reference herein in each of their entireties.

What is claimed is:

1. A portable infusion device comprising:
   a housing having a cavity, a first opening into the cavity, and a second opening into the cavity, the cavity having a curved portion;
   an elongate flexible member, the flexible member being positioned at least in part in the curved portion, the flexible member being substantially axially incompressible and laterally flexible;
   whereby, when a medication ampule including a piston is positioned adjacent to the first opening, the flexible member can be advanced through the curved portion of the cavity to push against and move the ampule piston without substantially compressing the flexible member;
   an ampule holder having a cavity sized to receive an ampule therein, a first opening into the ampule holder cavity, and a second opening into the ampule holder cavity, the ampule holder second opening positioned adjacent to the housing first opening; and
   a collar sized to receive a first portion of the ampule holder in the collar the ampule holder first positioned including the ampule holder first opening, wherein the collar is a split collar having an interior surface, a slot, and a groove on the interior surface, and the ampule holder includes an upstanding peg sized to be received in the groove.

2. A portable infusion device comprising:
   a housing having a cavity, a first opening into the cavity, and a second opening into the cavity, the cavity having a curved portion; and
   an elongate flexible member, the flexible member being positioned at least in part in the curved portion, the flexible member being substantially axially incompressible and laterally flexible;
   whereby, when a medication ampule including a piston is positioned adjacent to the first opening, the flexible member can be advanced through the curved portion of the cavity to push against and move the ampule piston without substantially compressing the flexible member, wherein the elongate flexible member comprises:
   an outer flexible member; and
   an intermediate flexible member positioned inside the outer flexible member.

3. An infusion device in accordance with claim 2, wherein the outer flexible member and the intermediate flexible member are not connected to each other along substantially their entire lengths.

4. An infusion device in accordance with claim 2, wherein the outer flexible member and the intermediate flexible member each include first and second end and are attached to each other at their first and second ends, respectively.

5. An infusion device in accordance with claim 2, further comprising an inner flexible member positioned inside the intermediate flexible member, the inner flexible member being substantially axially inextensible.

6. A portable infusion device comprising:
   a housing having a cavity, a first opening into the cavity, and a second opening into the cavity, the cavity having a curved portion;
   an elongate flexible member, the flexible member being positioned at least in part in the curved portion, the flexible member being substantially axially incompressible and laterally flexible;
   whereby, when a medication ampule including a piston is positioned adjacent to the first opening, the flexible member can be advanced through the curved portion of the cavity to push against and move the ampule piston without substantially compressing the flexible member, further comprising:
   a dosage sleeve at least partially positioned in the housing cavity and movable out of the housing second opening, the dosage sleeve including a hollow interior and an interior surface having threads; and
   a nut including an outer surface, a part of the nut outer surface including threads sized and configured to mate with the dosage sleeve threads, the nut attached to one end of the elongate flexible member;
   whereby rotation of the sleeve relative to the nut moves the sleeve away from the elongate flexible member.

7. An infusion device in accordance with claim 6, wherein the dosage sleeve further comprises:
   an exterior surface including a plurality of longitudinally extending grooves; and
   wherein the housing includes at least one peg sized and positioned to engage the dosage sleeve exterior surface and produce a click when the dosage sleeve is rotated.

8. An infusion device in accordance with claim 6, wherein the dosage sleeve includes an inner end inside the cavity and an outer end, and wherein the flexible member has a length so that when the nut is adjacent to dosage sleeve outer end a second end of the flexible member is immediately adjacent to the housing first opening.

9. An infusion device in accordance with claim 6, wherein the dosage sleeve further comprises an annular shoulder positioned at the dosage sleeve inner end, wherein the housing further comprises a shoulder adjacent to the dosage sleeve, and further comprising a spring positioned between the dosage sleeve shoulder and the housing shoulder, the spring being compressed when the dosage sleeve moves out of the housing.

10. An infusion device in accordance with claim 6, wherein the dosage sleeve further comprises a friction surface, wherein the housing further comprises a friction surface bearing against the dosage sleeve friction surface, and wherein the housing friction surface is configured and arranged so that the friction generated between the housing friction surface and the dosage sleeve friction surface is not constant as the dosage sleeve moves out of the housing.

11. An infusion device in accordance with claim 6, further comprising:
    a zero set sleeve positioned around a portion of the dosage sleeve, the zero set sleeve being rotatable on the dosage sleeve and including an annular ring;
    a zero set spring;
    wherein the dosage sleeve include an annular ring at the dosage sleeve outer end;

wherein the zero set spring is positioned between the zero set sleeve annular ring and the dosage sleeve annular ring to bias the zero set sleeve and the dosage sleeve together.

12. An infusion device in accordance with claim 11, wherein the zero set sleeve includes an outer surface and dosage indicia on the zero set sleeve outer surface; and further comprising a window through the housing, the zero set sleeve dosage indicia being visible through the window.

13. An infusion device in accordance with claim 6, further comprising a slot in the housing, an annular ring positioned around the dosage sleeve, an arm connected to the annular ring and extending through the slot, and a side injection actuator attached to the arm outside of the housing, wherein pushing on the side injection actuator pushes the dosage sleeve.

14. An infusion device in accordance with claim 6, wherein the dosage sleeve further comprises an inner end, an outer end, and a pair of slots extending longitudinally from the dosage sleeve inner end, the pair of slots forming a finger from a portion of the dosage sleeve;

wherein the housing cavity further comprises a recess adjacent to the housing second opening; and further comprising a locking member rotatably positioned in the recess, the locking member having a non-uniform exterior surface including first and second portions;

whereby when the locking member is positioned with the first portion immediately adjacent to the dosage sleeve finger, the first portion prevents the finger from flexing radially outward, and when the locking member is positioned with the second portion immediately adjacent to the dosage sleeve finger, the second portion permits the finger to flex radially outward.

15. An infusion device in accordance with claim 1, further comprising a locking cam movably mounted in the housing cavity, the cam positioned adjacent to the elongate flexible member, the locking cam being movable between a first orientation in which the locking cam does not interfere with movement of the flexible member in the cavity, and a second orientation in which the locking cam presses against the flexible member an inhibits movement of the flexible member in the cavity.

* * * * *